(12) United States Patent
Neil

(10) Patent No.: US 10,386,233 B2
(45) Date of Patent: Aug. 20, 2019

(54) VARIABLE RESOLUTION SPECTROMETER

(71) Applicant: KLA-TENCOR CORPORATION, Milpitas, CA (US)

(72) Inventor: Mark Allen Neil, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 16/226,597

(22) Filed: Dec. 19, 2018

(65) Prior Publication Data

US 2019/0212255 A1     Jul. 11, 2019

Related U.S. Application Data

(60) Provisional application No. 62/614,397, filed on Jan. 6, 2018.

(51) Int. Cl.
*G01J 3/02* (2006.01)
*G01J 3/06* (2006.01)
(Continued)

(52) U.S. Cl.
CPC .............. *G01J 3/12* (2013.01); *G01J 3/0202* (2013.01); *G01J 3/027* (2013.01); *G01J 3/0297* (2013.01);
(Continued)

(58) Field of Classification Search
CPC .... G01N 21/211; G01N 21/25; G01N 21/251; G01N 21/255; G01N 21/29; G01N 21/31; G01N 21/47; G01N 21/4788; G01N 21/55; G01N 21/8422; G01N 21/9501; G01N 2021/213; G01N 2021/214; G01N 2021/3711; G01N 2021/4711; G01B 11/02; G01B 11/024; G01B 11/06; G01B 11/0616; G01B 11/0625; G01B 11/0633; G01B 11/0641; G01B 11/065;
(Continued)

(56) References Cited

U.S. PATENT DOCUMENTS 5,608,526 A    3/1997   Piwonka-Corle et al.
5,859,424 A    1/1999   Norton et al.
(Continued)

OTHER PUBLICATIONS

ISA/KR, International Search Report for PCT/US2019/012226 dated Apr. 30, 2019.

*Primary Examiner* — Gordon J Stock, Jr.
(74) *Attorney, Agent, or Firm* — Hodgson Russ LLP

(57) ABSTRACT

Systems, methods, apparatuses, and articles of manufacture are provided for recovering a digitized spectrum and may comprise: an optical system configured to transform rays, the optical system including a diffraction grating, a steering mirror, a stage, and an actuator configured to move one of the stage, diffraction grating, or steering mirror according to a movement regime to vary an incidence of the rays on the stage; a sensor array disposed on the stage configured to receive the rays incident from the optical system at a plurality of measurement locations to obtain a plurality of ray spectra; and a processor electrically connected to the sensor array configured to receive the ray spectra, interleave the ray spectra to yield an interleaved spectrum, and deconvolve a point spread function corresponding to the optical system from the interleaved spectrum to yield a recovered digitized spectrum.

20 Claims, 12 Drawing Sheets

(51) Int. Cl.
*G01J 3/12* (2006.01)
*G01J 3/18* (2006.01)
*G01J 3/28* (2006.01)
*G02B 6/293* (2006.01)
G03F 7/20 (2006.01)
G01B 11/02 (2006.01)
G01B 11/14 (2006.01)
G01N 21/21 (2006.01)
G01N 21/47 (2006.01)
G01N 21/55 (2014.01)

(52) U.S. Cl.
CPC . *G01J 3/06* (2013.01); *G01J 3/18* (2013.01); *G01J 3/28* (2013.01); *G02B 6/29314* (2013.01); *G01B 11/02* (2013.01); *G01B 11/14* (2013.01); *G01J 2003/1282* (2013.01); *G01N 21/211* (2013.01); *G01N 21/47* (2013.01); *G01N 21/55* (2013.01); *G01N 2021/213* (2013.01); *G01N 2021/214* (2013.01); *G03F 7/70616* (2013.01)

(58) Field of Classification Search
CPC ......... G01B 11/08; G01B 11/14; G01B 11/22; G01B 11/24; G01B 11/30; G02B 6/2931; G02B 6/29313; G02B 6/29314; G01J 3/0202; G01J 3/021; G01J 3/0237; G01J 3/0262; G01J 3/027; G01J 3/0286; G01J 3/0297; G01J 3/06; G01J 3/12; G01J 3/18; G01J 3/28; G01J 3/2803; G01J 3/2823; G01J 3/46; G01J 3/50; G01J 2003/061; G01J 2003/062; G01J 2003/063; G01J 2003/066; G01J 2003/069; G01J 2003/1282; G01J 2003/2813; G03F 7/70616; G03F 7/70625; G03F 7/70633
See application file for complete search history.

(56) References Cited

U.S. PATENT DOCUMENTS

| | | | |
|---|---|---|---|
| 6,429,943 B1 | 8/2002 | Opsal et al. | |
| 6,654,516 B2* | 11/2003 | So | G02B 6/2931 385/11 |
| 6,842,549 B2* | 1/2005 | So | G02B 5/203 385/15 |
| 7,105,806 B2* | 9/2006 | Pappin | H01J 49/0036 250/282 |
| 7,478,019 B2 | 1/2009 | Zangooie et al. | |
| 7,933,026 B2 | 4/2011 | Opsal et al. | |
| 9,222,834 B2* | 12/2015 | Den Boef | G01J 3/4412 |
| 9,786,057 B2* | 10/2017 | Miyai | H04N 5/2256 |
| 9,958,327 B2* | 5/2018 | Shachaf | G01J 3/28 |
| 10,139,352 B2* | 11/2018 | Pandev | G01N 21/93 |
| 10,217,190 B2* | 2/2019 | Liu | G06T 3/4053 |
| 2002/0044280 A1 | 4/2002 | Weigold et al. | |
| 2003/0090783 A1* | 5/2003 | So | G02B 27/4233 359/337.11 |
| 2005/0276601 A1* | 12/2005 | Morawski | G01J 3/28 398/42 |
| 2007/0179729 A1* | 8/2007 | Morawski | G01J 3/02 702/104 |
| 2008/0165343 A1 | 7/2008 | Lewis et al. | |
| 2009/0225315 A1 | 9/2009 | Wilt et al. | |
| 2010/0004773 A1* | 1/2010 | Kochergin | G01N 21/211 700/103 |
| 2014/0354773 A1 | 12/2014 | Venkataraman et al. | |
| 2016/0047759 A1 | 2/2016 | Wang et al. | |
| 2017/0191945 A1* | 7/2017 | Zhang | G01N 21/8851 |

\* cited by examiner

VARIABLE RESOLUTION SPECTROMETER

CROSS REFERENCE TO RELATED APPLICATIONS

This application claims priority to U.S. Provisional Application No. 62/614,397, filed on Jan. 6, 2018, the entire disclosure of which is hereby incorporated by reference.

FIELD OF THE DISCLOSURE

The disclosure generally relates to improvements in semiconductor metrology. More particularly the disclosure generally relates to improvements in measurement of thin films, grating structures, and critical dimension structures.

BACKGROUND OF THE DISCLOSURE

Evolution of the semiconductor manufacturing industry is placing greater demands on yield management and, in particular, on metrology and inspection systems. Critical dimensions continue to shrink, yet the industry needs to decrease time for achieving high-yield, high-value production. Minimizing the total time from detecting a yield problem to fixing it determines the return-on-investment for a semiconductor manufacturer.

Fabricating semiconductor devices, such as logic and memory devices, typically includes processing a semiconductor wafer using a large number of fabrication processes to form various features and multiple levels of the semiconductor devices. For example, lithography is a semiconductor fabrication process that involves transferring a pattern from a reticle to a photoresist arranged on a semiconductor wafer. Additional examples of semiconductor fabrication processes include, but are not limited to, chemical-mechanical polishing (CMP), etch, deposition, and ion implantation. Multiple semiconductor devices may be fabricated in an arrangement on a single semiconductor wafer and then separated into individual semiconductor devices.

Metrology may be used during semiconductor manufacturing to take various measurements of, for example, a semiconductor wafer or reticle. Metrology tools can be used to measure structural and material characteristics associated with various semiconductor fabrication processes. For example, the metrology tools can measure material composition or can measure dimensional characteristics of structures and films such as film thickness, critical dimension (CD) of structures, or overlay. These measurements are used to facilitate process controls and/or yield efficiencies during the manufacture of semiconductor dies.

As semiconductor device pattern dimensions continue to shrink, smaller metrology targets are often required. Furthermore, the requirements for measurement accuracy and matching to actual device characteristics increase the need for device-like targets as well as in-die and even on-device measurements. Various metrology implementations have been proposed to achieve that goal. For example, focused beam ellipsometry based on primarily reflective optics has been proposed. Apodizers can be used to mitigate the effects of optical diffraction causing the spread of the illumination spot beyond the size defined by geometric optics. The use of high-numerical-aperture tools with simultaneous multiple angle-of-incidence illumination is another way to achieve small-target capability.

Other measurement examples may include measuring the composition of one or more layers of the semiconductor stack, measuring certain defects on (or within) the wafer, and measuring the amount of photolithographic radiation exposed to the wafer. In some cases, a metrology tool and algorithm may be configured for measuring non-periodic targets.

Measurement of parameters of interest usually involves a number of algorithms. For example, optical interaction of the incident beam with the sample is modeled using electromagnetic (EM) solver and uses such algorithms as rigorous coupled-wave analysis (RCWA), finite element method (FEM), method of moments, surface integral method, volume integral method, finite-difference time-domain (FDTD), and others. The target of interest is usually modeled (parametrized) using a geometric engine, or in some cases, process modeling engine or a combination of both. A geometric engine is implemented in these cases.

Collected data can be analyzed by a number of data fitting and optimization techniques an technologies including libraries; Fast-reduced-order models; regression; machine-learning algorithms such as neural networks, support-vector machines (SVM); dimensionality-reduction algorithms such as, e.g., principal component analysis (PCA), independent component analysis (ICA), and local-linear embedding (LLE); sparse representation such as Fourier or wavelet transform; Kalman filters; algorithms to promote matching from same or different tool types; and others.

Collected data can also be analyzed by algorithms that do not include modeling, optimization and/or fitting.

Computational algorithms are usually optimized for metrology applications with one or more approaches being used such as design and implementation of computational hardware, parallelization, distribution of computation, load-balancing, multi-service support, dynamic load optimization, etc. Different implementations of algorithms can be done in firmware, software, field-programmable gate array (FPGA), programmable optics components, etc.

The data analysis and fitting steps usually pursue one or more of: (1) measurement of CD, sidewall angle (SWA), shape, stress, composition, films, bandgap, electrical properties, focus/dose, overlay, generating process parameters (e.g., resist state, partial pressure, temperature, focusing model), and/or any combination thereof; (2) modeling and/or design of metrology systems; and (3) modeling, design, and/or optimization of metrology targets.

In the presently available film measurement systems, an illuminating beam of light passes first through the film stack to be measured and then through a grating or prism. An image of the resulting spectrum is produced on a sensor comprising an array of pixels, which are digitized and conveyed to a computing engine. The computing engine uses modeling techniques to determine the properties of the film stack, such as the thickness or material properties of each layer.

One problem these systems exhibit is that their spectral resolutions are limited by their optical point spread functions (PSFs) and sensor pixel sizes. The problem is aggravated when measuring thick film stacks, such as high aspect ratio (HAR) devices, for example, 3D-Flash, when the width of the PSF is larger than the period of the spectral signal. Such a signal is then further attenuated as it is quantized into individual pixels that are also of a similar order to the period of the spectral signal.

These attenuating effects are typically deconvolved from the signal prior to solving for film stack parameters, as modelling these effects is costly in computing resources. However, deconvolution fails to correctly reconstruct the ideal spectrum with thick film stacks. This failure is most evident in the shorter wavelengths like ultraviolet.

Additionally, thick film stacks produce high frequency responses for shorter wavelengths. Conventional techniques are unable to reconstruct the ideal spectrum for post-processing. Computing engines using the conventional techniques cannot correctly determine the underlying film stack properties. This greatly diminishes the effectiveness of the inspection tool.

The present disclosure overcomes these and other limitations, thus improving the ability of an inspection tool to measure new types of film stacks.

SUMMARY OF THE DISCLOSURE

In an embodiment of the present disclosure, a variable resolution spectrometer is provided comprising an optical system configured to transform rays, a sensor on a stage, an actuator, and a processor. The optical system may include a diffraction grating, a steering mirror, a stage, and an actuator configured to move one of the stage, diffraction grating, or steering mirror according to a movement regime to vary an incidence of the rays on the stage. The movement regime may include a start position and an end position. The variable resolution spectrometer may further include a sensor array disposed on the stage and include a plurality of pixel columns. The sensor array may be configured to receive the rays incident from the optical system at a plurality of measurement locations to obtain a plurality of ray spectra. Each pixel column may have at least one pixel. The variable resolution spectrometer may further include a processor electrically connected to the sensor array. The processor may be further configured to receive the ray spectra, interleave the ray spectra to yield an interleaved spectrum, and deconvolve a point spread function corresponding to the optical system from the interleaved spectrum to yield a recovered digitized spectrum.

In another embodiment, the present disclosure may be embodied as a method for recovering a digitized spectrum. Such a method may comprise providing an optical system configured to transform rays, executing a scan operation, and using a processor to process ray spectra into a digitized spectrum. The optical system may include a diffraction grating, a steering mirror, an actuator, and a stage. The scan operation may include moving, using the actuator, one of the stage, diffraction grating, or steering mirror according to a movement regime to vary an incidence of the rays on the stage and sensing, using a sensor array, rays incident on the sensor array from the optical system at a plurality of measurement locations to obtain a plurality of ray spectra, wherein each of the pixel columns has at least one pixel. The movement regime may have a start position and an end position. The sensor array may be disposed on the stage and may include a plurality of pixel columns. At the processor, ray spectra may be received, the ray spectra may be interleaved to yield an interleaved spectrum, and a point spread function corresponding to the optical system may be deconvolved from the interleaved spectrum to yield a recovered digitized spectrum.

In another embodiment, the present disclosure may be embodied as a non-transitory computer-readable storage medium, comprising one or more programs for executing steps on one or more computing devices. The steps may include receiving ray spectra obtained from rays incident on a sensor array, interleaving the ray spectra to yield an interleaved spectrum, and deconvolving a point spread function corresponding to the optical system from the interleaved spectrum to yield a recovered digitized spectrum. The sensor array may include a plurality of pixel columns, and each of the pixel columns may have at least one pixel. The sensor array may be disposed on a stage. The ray spectra may be received from an optical system comprising a stage, a diffraction grating and a steering mirror, wherein the stage, diffraction grating, or steering mirror may be moved using an actuator according to a movement regime to vary the incidence of rays on the stage. Such a movement regime may have a start position and an end position.

The actuator may be a piezo-actuator, a servo motor, a stepper motor, or another suitable actuator.

In an embodiment, the stage may be moved by an actuator according to an incremental translation movement regime. In an incremental translation movement regime, the stage may be translatably moved in one or more increments along a linear path from the start position to the end position, and each of the increments may have a start point and an end point separated by an incremental linear distance that is less than a total linear distance between a start position and an end position.

In an embodiment, the stage may be moved by an actuator according to a continuous translation movement regime. In a continuous translation movement regime, the stage may be translatably moved substantially continuously along a linear path from a start position to an end position.

In an embodiment, the stage may be moved by an actuator according to an incremental rotation movement regime. In an incremental translation movement regime, the stage may be rotatably moved in one or more increments along an arcuate path from the start position to the end position, and each of the increments may have a start point and an end point separated by an incremental arc length that is less than a total arc length between a start position and an end position.

In an embodiment, the stage may be moved by an actuator according to a continuous rotation movement regime. In a continuous rotation movement regime, the stage may be rotatably moved substantially continuously along an arcuate path from a start position to an end position.

In an embodiment, the diffraction grating may be moved by an actuator according to an incremental translation movement regime. In an incremental translation movement regime, the diffraction grating may be translatably moved in one or more increments along a linear path from the start position to the end position, and each of the increments may have a start point and an end point separated by an incremental linear distance that is less than a total linear distance between a start position and an end position.

In an embodiment, the diffraction grating may be moved by an actuator according to a continuous translation movement regime. In a continuous translation movement regime, the diffraction grating may be translatably moved substantially continuously along a linear path from a start position to an end position.

In an embodiment, the diffraction grating may be moved by an actuator according to an incremental rotation movement regime. In an incremental translation movement regime, the diffraction grating may be rotatably moved in one or more increments along an arcuate path from the start position to the end position, and each of the increments may have a start point and an end point separated by an incremental arc length that is less than a total arc length between a start position and an end position.

In an embodiment, the diffraction grating may be moved by an actuator according to a continuous rotation movement regime. In a continuous rotation movement regime, the diffraction grating may be rotatably moved substantially continuously along an arcuate path from a start position to an end position.

In an embodiment, the steering mirror may be moved by an actuator according to an incremental translation movement regime. In an incremental translation movement regime, the steering mirror may be translatably moved in one or more increments along a linear path from the start position to the end position, and each of the increments may have a start point and an end point separated by an incremental linear distance that is less than a total linear distance between a start position and an end position.

In an embodiment, the steering mirror may be moved by an actuator according to a continuous translation movement regime. In a continuous translation movement regime, the steering mirror may be translatably moved substantially continuously along a linear path from a start position to an end position.

In an embodiment, the steering mirror may be moved by an actuator according to an incremental rotation movement regime. In an incremental translation movement regime, the steering mirror may be rotatably moved in one or more increments along an arcuate path from the start position to the end position, and each of the increments may have a start point and an end point separated by an incremental arc length that is less than a total arc length between a start position and an end position.

In an embodiment, the steering mirror may be moved by an actuator according to a continuous rotation movement regime. In a continuous rotation movement regime, the steering mirror may be rotatably moved substantially continuously along an arcuate path from a start position to an end position.

Two measurement locations within the plurality of measurement locations may be separated by a distance less than a pixel breadth.

The sensor array may be a charge-coupled device (CCD).

BRIEF DESCRIPTION OF THE FIGURES

For a fuller understanding of the nature and objects of the disclosure, reference should be made to the following detailed description taken in conjunction with the accompanying drawings, in which.

DETAILED DESCRIPTION OF THE DISCLOSURE

Figure 1:
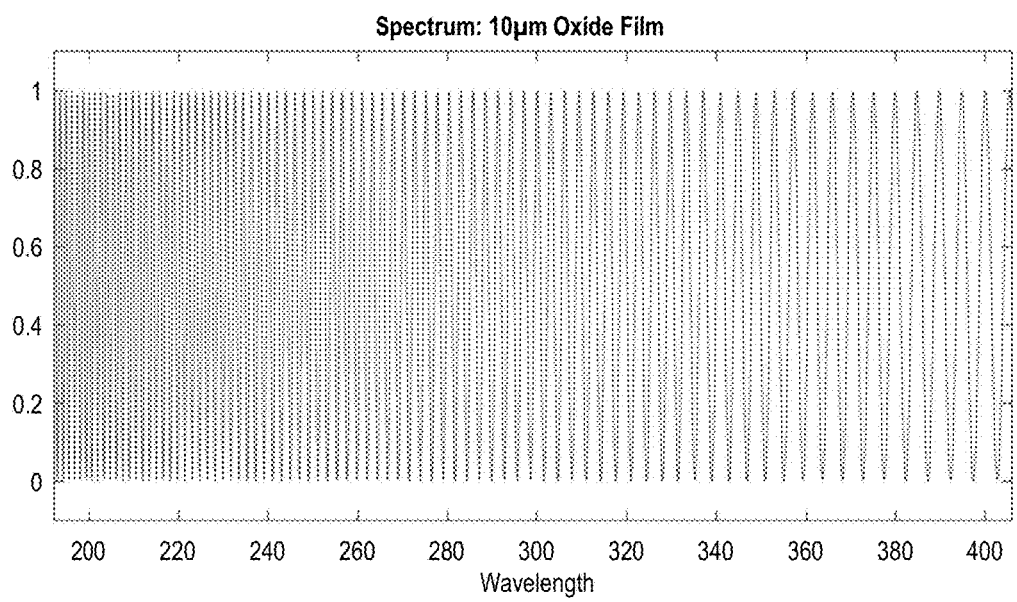
FIG. 1 is an ideal reflectometer spectrum.

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

Embodiments disclosed herein address the challenges of thick-film measurements, including measurements of three-dimensional flash (3D-Flash) film stacks. Improvements in the measurement of thin films, grating, and CD structures may also be realized using embodiments of the present disclosure. The techniques, methods, and apparatuses disclosed herein may be implemented both in reflectometer and ellipsometer measurement system, and in other appropriate metrology systems.

Embodiments of a metrology tool may comprise an illumination system that illuminates a target, a collection system that captures relevant information provided by the illumination system's interaction, or lack thereof, with a target, device, or feature, and a processing system that analyzes the information collected using one or more algorithms. Metrology tools can be used to measure structural and material characteristics (e.g., material composition, dimensional characteristics of structures and films such as film thickness and/or critical dimensions of structures, overlay, etc.) associated with various semiconductor fabrication processes. These measurements may be used to facilitate process controls and/or yield efficiencies in the manufacture of semiconductor dies.

A metrology tool in accordance with embodiments of the present disclosure can comprise one or more hardware configurations, which may be used in conjunction with certain embodiments of the present disclosure to, for example, measure the various aforementioned semiconductor structural and material characteristics. Examples of such hardware configurations include, inter alia: (1) spectroscopic ellipsometers (SEs); (2) SEs with multiple angles of illumination; (3) SEs measuring Mueller matrix elements (e.g. using rotating compensator(s)); (4) single-wavelength ellipsometers; (5) beam profile ellipsometers (angle-resolved ellipsometers); (6) beam profile reflectometers (angle-resolved reflectometer); (7) broadband reflective spectrometers (spectroscopic reflectometers); (8) Single-wavelength reflectometers; (9) angle-resolved reflectometers; (10) imaging systems; and (11) scatterometers (e.g. speckle analyzers).

Hardware configurations can be separated into discrete operational systems. Alternately, one or more hardware configurations can be combined into a single tool. In addition, there may be numerous optical elements, including lenses, collimators, mirrors, quarter-wave plates, polarizers, detectors, cameras, apertures, and/or light sources. Wavelengths can vary from about 120 nm to 3 microns. For non-ellipsometer systems, signals collected can be polarization-resolved or unpolarized. In many cases, multiple metrology tools can be used for measurements on a single or multiple metrology targets.

An illumination system according to some embodiment of the present disclosure can include one or more light sources. Such a light source may generate light having only one wavelength (i.e., monochromatic light), light having a number of discrete wavelengths (i.e., polychromatic light), light having multiple wavelengths (i.e., broadband light) and/or light the sweeps through wavelengths, either continuously or hopping between wavelengths (i.e. tunable sources or swept source). Examples of suitable light sources are: a white light source, an ultraviolet (UV) laser, an arc lamp or an electrode-less lamp, a laser sustained plasma (LSP) source, a super-continuum source (such as a broadband laser source), or shorter-wavelength sources such as x-ray sources, extreme UV sources, or some combination thereof. The light source may also be configured to provide light having sufficient brightness, which in some cases may be a brightness greater than about 1 W/(nm cm2 Sr). The metrology system may also include a fast feedback to the light source for stabilizing its power and wavelength. Output of the light source can be delivered via free-space propagation, or in some cases delivered via optical fiber or light guide of any type.

The metrology tool may be designed to make many different types of measurements related to semiconductor manufacturing. Certain embodiments of the present disclosure may be applicable to such measurements. For example, in certain embodiments, the tool may measure characteristics of one or more targets, such as critical dimensions, overlay, sidewall angles, film thicknesses, process-related parameters (e.g., focus and/or dose). The targets can include certain regions of interest that are periodic in nature, such as for example gratings in a memory die. Targets can include multiple layers, or films, whose thicknesses can be measured by the metrology tool. Targets can include target designs placed, or already existing, on the semiconductor wafer for use, e.g., with alignment and/or overlay registration operations. Certain targets can be located at various places on the semiconductor wafer. For example, targets can be located within the scribe lines (e.g., between dies) and/or located in the die itself. In certain embodiments, multiple targets are measured (at the same time or at differing times) by the same or multiple metrology tools. The data from such measurements may be combined. Data from the metrology tool may be used in the semiconductor manufacturing process, for example, to feed-forward, feed-backward, and/or feed-sideways corrections to the process (e.g. lithography, etch) and therefore, might yield a complete process control solution.

Figure 2:
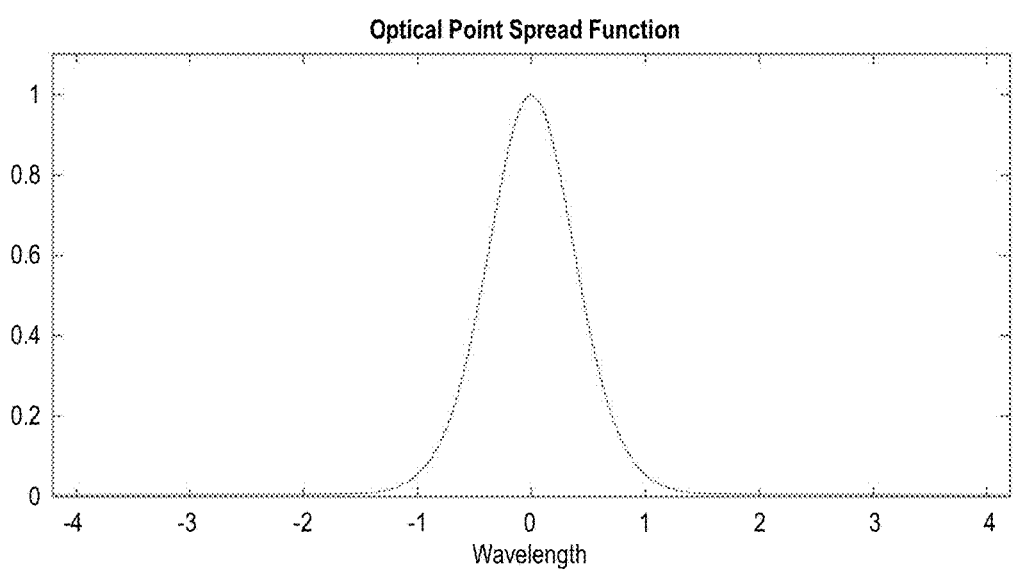
FIG. 2 is an optical point-spread function.
Figure 3:
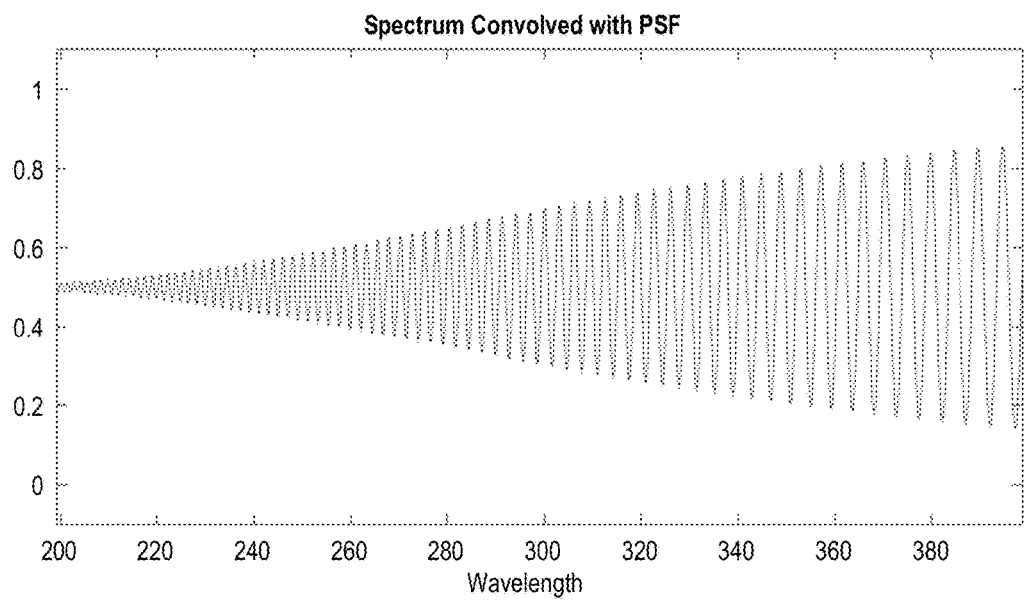
FIG. 3 is an ideal reflectometer spectrum with an optical point-spread function applied.
Figure 4:
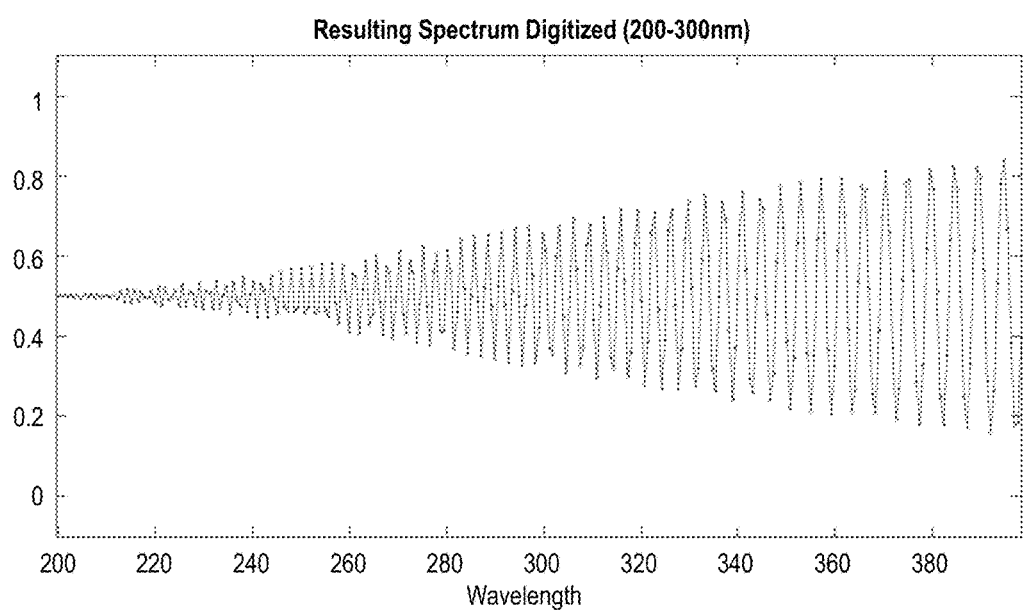
FIG. 4 is a digitized spectrum resulting from digitizing an ideal reflectometer spectrum with an optical point-spread function applied (200-300 nm)
Figure 5:
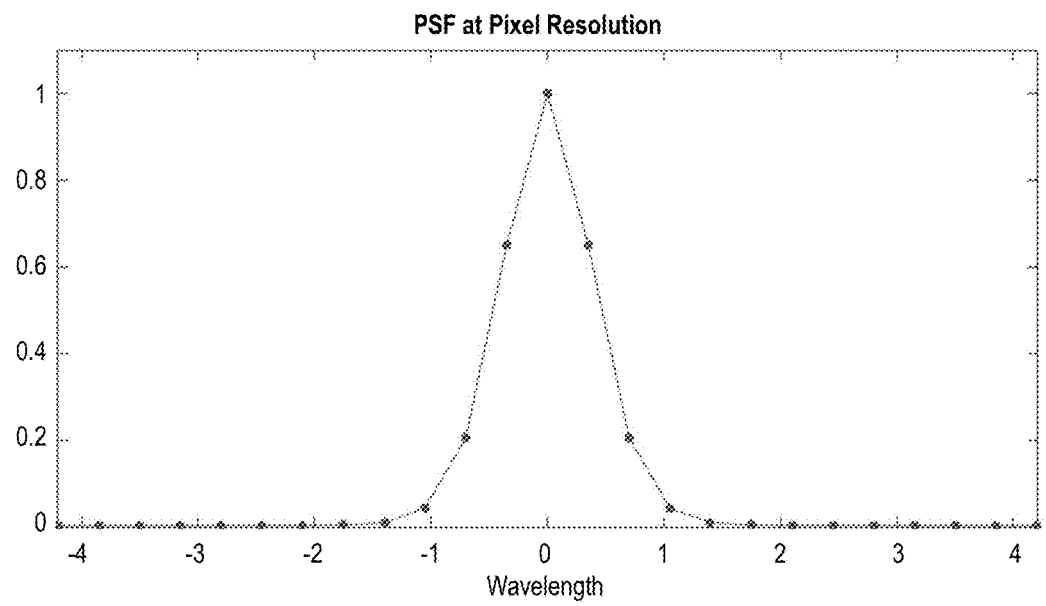
FIG. 5 is a reflectometer point-spread function at pixel resolution.

FIGS. 1-6 graphically show an exemplary process of signal reconstruction. FIG. 1 shows an ideal spectrum, as would be received as light rays from a wafer by an example reflectometer. FIG. 2 shows the optical PSF for the example reflectometer's optics. The ideal spectrum shown in FIG. 1 is convolved with the optical PSF shown in FIG. 2 as the rays pass through the reflectometer, resulting in the convolved (blurred) spectrum, shown in FIG. 3. This blurred spectrum is digitized, or quantized, into a digital blurred spectrum, shown in FIG. 4, as the rays, having passed through the optics of the reflectometer, fall incident on the sensor pixels. From the digital blurred spectrum of FIG. 4, the digital point spread function matching its resolution, shown in FIG. 5, is deconvolved to recover the deconvolved digital spectrum, shown compared to the original ideal spectrum in FIG. 6.

Figure 6:
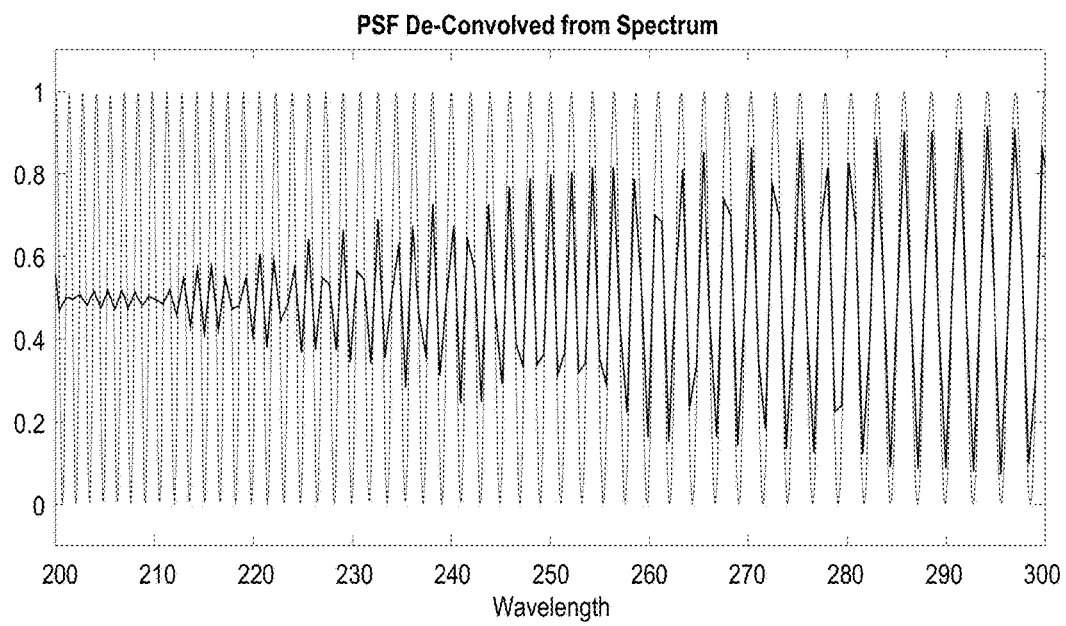
FIG. 6 is a recovered digitized spectrum with a point spread function at pixel resolution deconvolved.

As can been observed in the recovered spectrum depicted in FIG. 6, this method does not adequately recover the original spectrum.

One embodiment of the present disclosure solves this problem by mounting a sensor array to a high-precision motion stage. The motion stage may then translate or rotate the sensor array along the wavelength axis of the impinging rays. In other embodiments of the present disclosure, the sensor array is mounted to a fixed stage, and a steering mirror or diffraction grating is translated or rotated to modify the incidence of the impinging rays.

Figure 7:
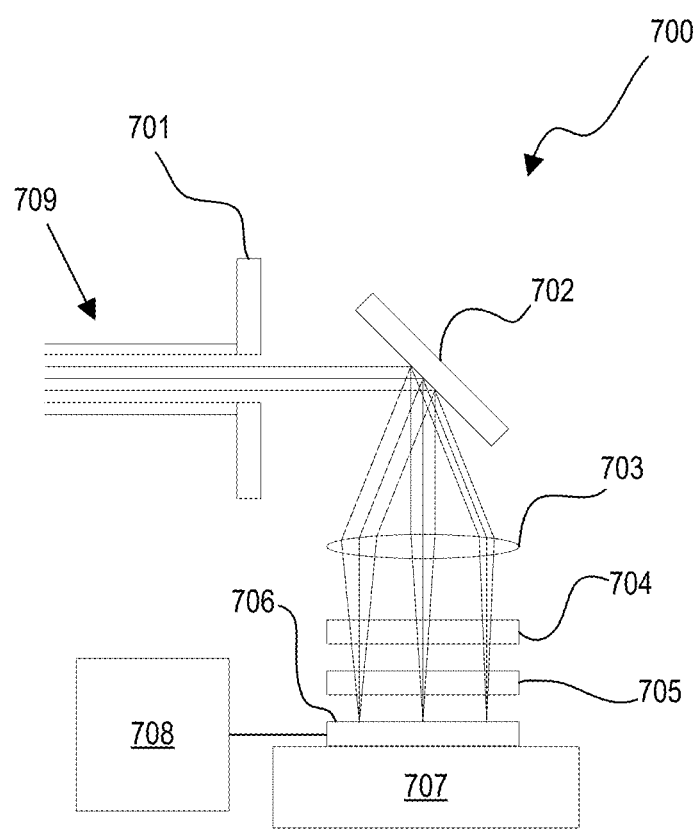
FIG. 7 is a spectrometer with a sensor mounted to a stage.

FIG. 7 depicts an exemplary embodiment of a variable resolution spectrometer 700 according to the present disclosure. Variable resolution spectrometer 700 may comprise an optical system, which may include aperture stop 701, diffraction grating 702, focusing lens 703, steering mirror 704, order sorting filter 705, and stage 707. Sensor array 706 may be mounted to stage 707. Sensor array 706 may be in communication with processor 708. Such communication may be over a communication link, which may be embodied as any suitable means, such as a digital signal carrier wire or other suitable means, whether wired or wireless. Such a communication link may be digital or analog. In some embodiments, the communication link is a wired Ethernet link over TCP/IP. In some embodiments, an analog/digital signal converter is employed.

In a static state, aperture stop 701 may be positioned such that it receives rays 709 from the wafer. Aperture stop 701 may block a portion of rays 709 and may permit a portion of rays 709 to pass through to diffraction grating 702. At diffraction grating 702, rays 709 may be broken into its respective component wavelengths and directed towards focusing lens 703. At focusing lens 703, rays 709 may be focused at sensor array 706. After passing through focusing lens 703, rays 709 may pass through steering mirror 704, followed by order sorting filter 705. Rays 709, after having passed through the optical components, may fall incident on sensor 706, which is mounted to stage 707. At sensor 706, rays may be sensed and converted to an electrical signal, which may then be sent to processor 708.

Aperture stop 701 may be configured to permit only a portion of the rays 709 to pass through it into the remainder of the optical system. Aperture stop 701 may be a fixed or variable aperture stop, or an iris.

Diffraction grating 702 may be configured to diffract incident rays 709 into their component wavelengths. Diffraction grating 702 may also be positioned such that the optical axis is directed towards the remainder of the optical system, beginning with, for instance, focusing lens 703. In one embodiment, diffraction grating 702 is angled such that the optical axis post-diffraction grating is offset ninety degrees from the optical axis pre-diffraction grating. In some embodiments, the optical axis post-diffraction grating is selected based on the desired packaging of the system 700.

Order sorting filter 705 may be configured to selectively block diffraction orders greater than, for example, one. In some embodiments, when, for example, the 200 nm component of the light incident on diffraction grating 702 produces multiple diffraction orders, order sorting filter 705 permits only the first diffraction order of the 200 nm component of the light diffracted to pass through to the pixel(s) of sensor array 706 that receive 200 nm light.

Stage 707 may be positioned such that, in an instance, the optical axis post-diffraction grating is normal to it. Alternately, stage 707 may be positioned such that the optical axis post diffraction grating is collinear with an axis through it.

In an embodiment, sensor array 706 comprises a plurality of pixels. Pixels may be comprised of sub-pixels. Pixels may be elliptical or rectangular. In the case of elliptical or circular pixels, pixel breadth may be defined as a chord, which may be the major axis or minor axis in the case of an ellipse or diameter in the case of a circle. In the case of rectangular or square pixels, pixel breadth may be defined as a line segment that intersects two different edges of the rectangular or square pixel. In any instance, a pixel breadth may be a line segment intersecting the outermost perimeter of the pixel at two distinct points: a beginning point and an end point.

The pixels of sensor array 706 are arranged into a plurality of pixel columns with each pixel column having at least one pixel. Such an arrangement may form columns of pixel rows in sensor array 706. In the case of sensor array 706 being a one-dimensional, or linear, sensor, sensor array 706 may have n columns of rows, each row having one pixel, forming an n×1 pixel array. In the case of sensor array 706 being a two-dimensional sensor, sensor array 706 may have n columns of m pixels, forming an n×m pixel array.

Sensor array 706 may be embodied as a charge-coupled device (CCD). Alternatively, sensor array 706 may be embodied as another type of image sensor, e.g., active pixel sensors in complementary metal oxide semiconductor (CMOS) or N-type metal-oxide-semiconductor (NMOS) chips, or flat panel detectors.

Each ray in rays 709 may impinge, with an incidence, on sensor array 706 at a point of incidence and with an angle of incidence. The incidence of each ray may be described by a position and an angle of incidence.

Figure 8:
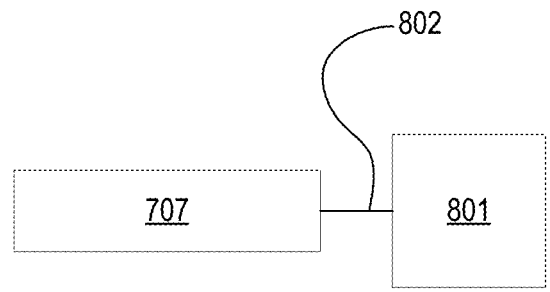
FIG. 8 is an actuatable stage.

FIG. 8 depicts an embodiment of the present disclosure wherein an actuator 801 is operatively connected by a transmission linkage 802 to the stage 707. In this embodiment, the stage 707 is a driven component.

Figure 9:
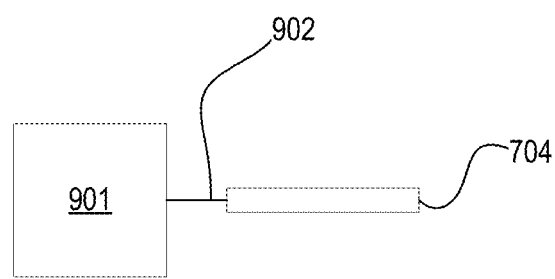
FIG. 9 is an actuatable steering mirror.

FIG. 9 depicts an embodiment of the present disclosure wherein an actuator 901 is operatively connected by a transmission linkage 902 to the steering mirror 704. In this embodiment, the steering mirror 704 is a driven component.

Figure 10:
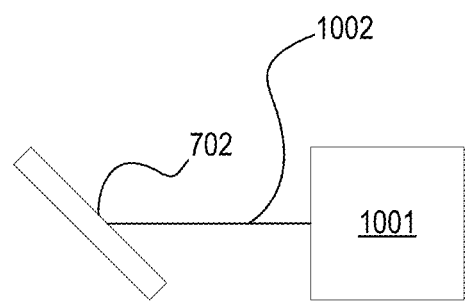
FIG. 10 is an actuatable diffraction grating.

FIG. 10 depicts an embodiment of the present disclosure wherein an actuator 1001 is operatively connected by a transmission linkage 1002 to the diffraction grating 702. In this embodiment, the diffraction grating 702 is a driven component.

In embodiments according to FIGS. 7-10, the driven component, stage 707, diffraction grating 702, or steering mirror 704, is driven by actuator 801, 901, or 1001, respectively, in an incremental movement regime. In these embodiments, the stage 707, diffraction grating 702, or steering mirror 704 begins positioned at a nominal home position where the post-diffraction grating optical axis intersects the sensor array 706 at a start position. The sensor array 706 acquires data for a fixed exposure time at a measurement location in an acquiring step. The data are then transferred to the processor 708 and stored in a storing step. The stage 707, diffraction grating 702, or steering mirror 704 is then moved translatably or rotatably such that the post-diffraction grating optical axis intersecting sensor array 706 has changed a fractional amount of a pixel breadth. The acquiring step, storing step, and moving step are then repeated until a set number of repetitions have been achieved in some embodiments. In other embodiments, the acquiring step, storing step, and moving step are then repeated until the point of intersection of the sensor array 706 and post-diffraction grating optical axis has moved to an end position, for example, an entire pixel breadth relative to its original location. In some embodiments, the fractional amount of a pixel breadth is one-tenth of a pixel and the number of repetitions is ten.

In other embodiments according to FIGS. 7-10, the driven component, stage 707, diffraction grating 702, or steering mirror 704, is driven by actuator 801, 901, or 1001, respectively, in a continuous movement regime. In this embodiment, the stage 707, diffraction grating 702, or steering mirror 704 begins positioned at a nominal home position. The sensor array 706 acquires data for a fixed exposure time at an initial measurement location in an initial acquiring step. The stage 707, diffraction grating 702, or steering mirror 704 begins moving substantially continuously translatably or rotatably. The sensor array 706 acquires data at a defined fractional amount of a pixel breadth (each a measurement location) for a fixed exposure time in an in-motion acquiring step. The data are then transferred to the processor 708 and stored in a storing step. The in-motion acquiring step and storing step are then repeated until a set number of repetitions have been achieved in some embodiments. In other embodiments, the in-motion acquiring step and storing step are then repeated until the point of intersection of the sensor array 706 and post-diffraction grating optical axis has moved to an end position, for example, an entire pixel breadth relative to its original location. In some embodiments, the number of repetitions is ten.

A number of measurements ($\Phi$) is defined based on how many measurements are taken between the start position and the end position, for example, the number of measurements taken over one pixel. For example, a typical $\Phi$ could be 2, 4, 8, 10, 16, or another integer. The number of measurements, the start position, and the end position may be used to determine the number of measurements in a plurality of measurement locations.

In some embodiments, the fractional amount of a pixel breadth is less than one pixel breadth, for example, one tenth of a pixel breadth. In other embodiments, the fractional amount of a pixel breadth is greater than one pixel breadth.

Actuators 801, 901, and 1001 may be embodied as, inter alia, a piezo actuator, a servo motor, or a stepper motor capable of sub-micron movement or positioning. Transmission linkages 802, 902, and 1002 may be embodied as any means for transferring an actuation force from an actuator to result in the translation or rotation, as appropriate, of the driven component. For instance, a piezo actuator may be used to actuate the driven component by means of a direct transmission linkage to translate the driven component or a cam transmission linkage to rotate the driven component. In another instance, a servo motor or stepper motor is operatively connected to the driven component by a transmission linkage embodied as a belt, rack-and-pinion, or cam to translate the driven component, or by a transmission linkage embodied as a shaft, which may be connected to a gearbox to rotate the driven component.

Figure 11:
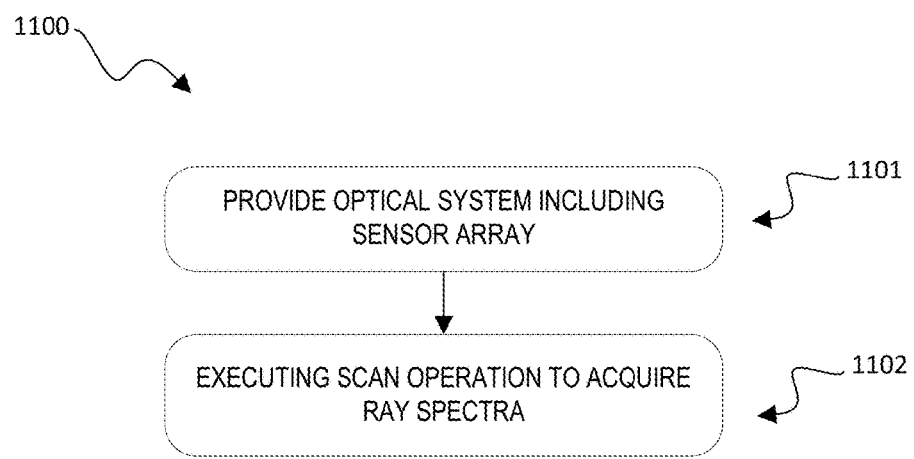
FIG. 11 is an embodiment method 1100 of acquiring ray spectra.

FIG. 11 shows an embodiment method 1100 of acquiring data in the form of ray spectra using optical system 700. At step 1101, an optical system is provided, including an aperture stop, a diffraction grating, a focusing lens, a steering mirror, an order sorting filter; and, an actuator, a stage, and a sensing array. At step 1102, a scan operation is executed to acquire scan data. The scan operation may include moving, using the actuator, one of the stage, diffraction grating, or steering mirror according to a movement regime to vary an incidence of the rays on the stage, the movement regime having a start position and an end position, and sensing, using a sensor array disposed on the stage including a plurality of pixel columns, each pixel column having at least one pixel, rays incident on the sensor array from the optical system at a plurality of measurement locations to obtain a plurality of ray spectra.

Figure 12:
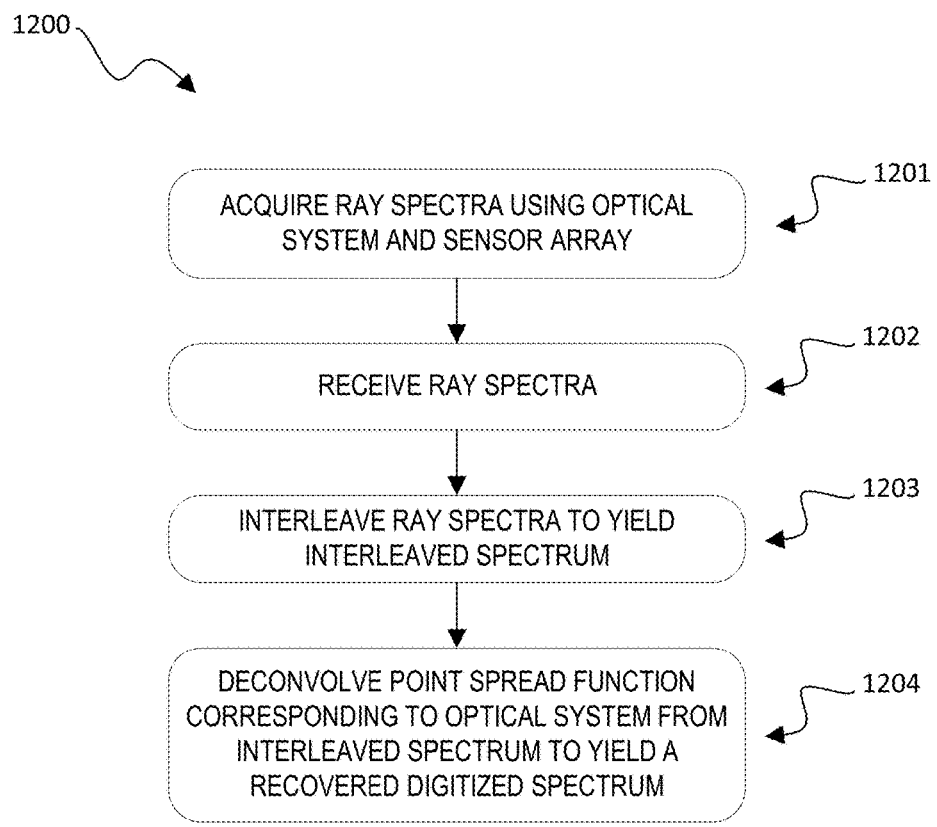
FIG. 12 is an embodiment method 1200 of processing ray spectra.
Figure 13:
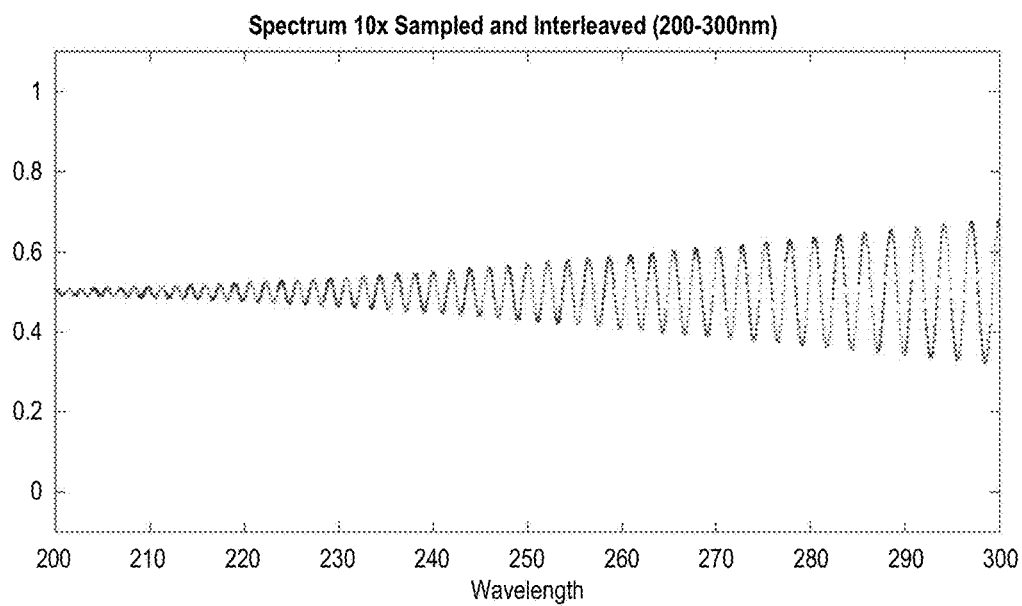
FIG. 13 is a 10× sample spectrum interleaved.
Figure 14:
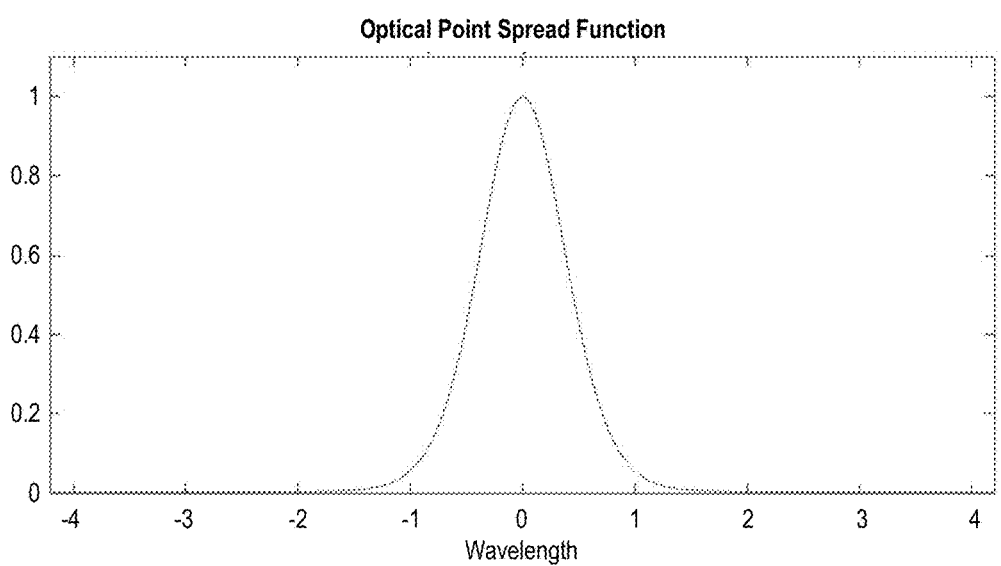
FIG. 14 is a 10× point-spread function at 10× pixel resolution.
Figure 15:
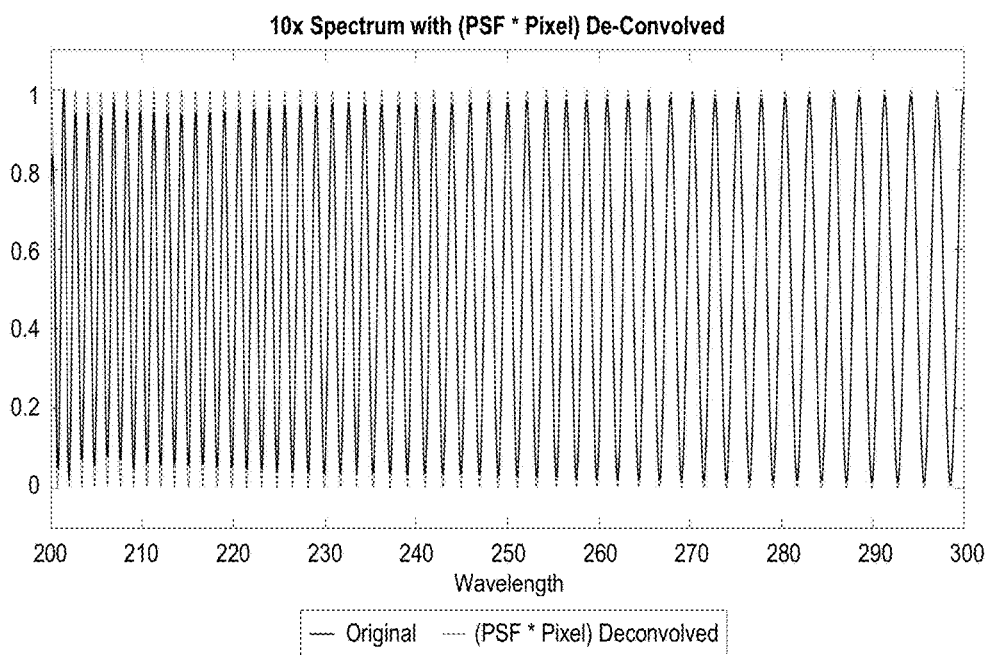
FIG. 15 is a 10× spectrum with a point-spread function at 10× pixel resolution deconvolved.
Figure 16:
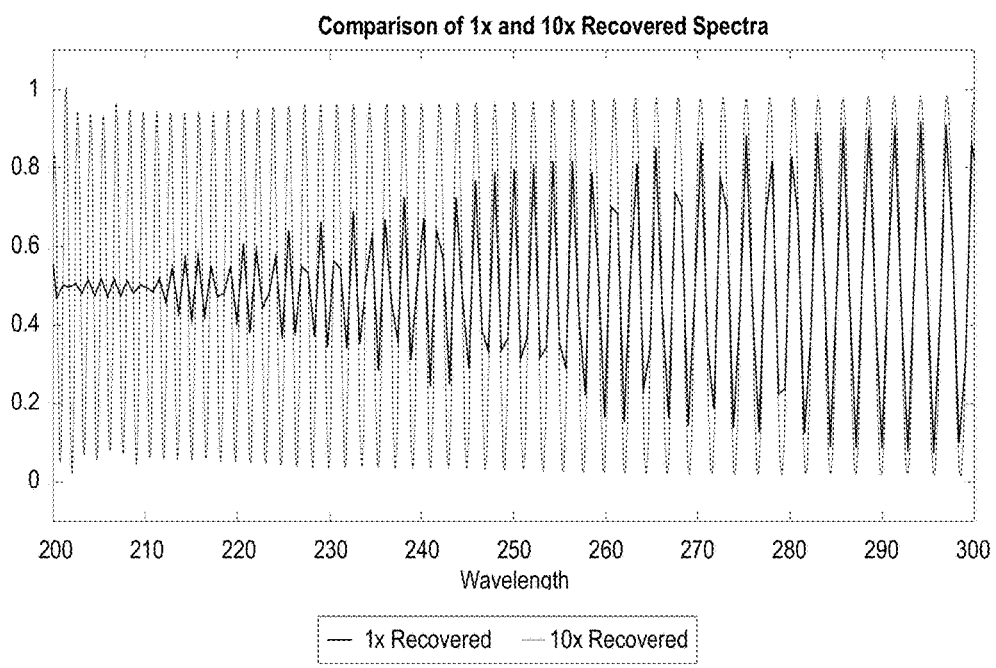
FIG. 16 is a comparison of 1× and 10× recovered spectra.

FIG. 12 shows an embodiment method 1200 of acquiring and processing the data received in the form of ray spectra received by processor 708. At step 1201, ray spectra are acquired using the optical system and sensor array as described herein. In some embodiments of the method 1200, ray spectra are acquired in accordance with method 1100. At step 1202, the ray spectra are received by the processor 708. At step 1203, the ray spectra are interleaved to yield an interleaved spectrum representing a resolution multiplier of the sensor array. This interleaved spectrum is shown for example in FIG. 13, for example, for $\Phi=10$. In FIG. 13, gaps are shown for each measurement location of the interleave. At step 1204, the point spread function corresponding to the optical system (also representing the resolution multiplier), exemplified in FIG. 14 for $\Phi=10$, is deconvolved interleaved spectrum to yield a recovered digitized spectrum. The recovered digitized spectrum is at a resolution that is higher than the actual resolution of the sensor array. The recovered digitized spectrum for example at $\Phi=10$, is shown compared to its original reflectometer ideal spectrum in FIG. 15.

For example, interleaving based on $\Phi=4$ may involve designating each of four measurements $A_1$ to $A_4$. Each may have N pixels, so we can label the individual pixels in acquisition "X" as $A_{X,1}$ to $A_{X,N}$. With these 4 acquisitions of N pixels, the interleaved spectrum may then have 4×N pixels, comprised of pixels: $A_{1,1}, A_{1,2}, A_{1,3}, A_{1,4}, \ldots, A_{N,1}, A_{N,2}, A_{N,3}, A_{N,4}$.

In an embodiment of the present disclosure, ray spectra are acquired based on ten measurement points per pixel, or $\Phi=10$.

Processor 708 may be embodied as a computer subsystem that includes a processor and an electronic data storage unit. The processor 708 may include a microprocessor, a microcontroller, or other devices.

The processor 708 may be coupled to the sensor array 706 in any suitable manner (e.g., via one or more transmission media, which may include wired and/or wireless transmission media) such that the processor 708 can receive output. The processor 708 may be configured to perform a number of functions using the output. The system 700 can receive instructions or other information from the processor 708. The processor 708 optionally may be in electronic communication with another wafer inspection tool, a wafer metrology tool, or a wafer review tool (not illustrated) to receive additional information or send instructions. For example, the processor 708 can be in electronic communication with a scanning electron microscope.

The processor 708, other system(s), or other subsystem(s) described herein may be part of various systems, including a personal computer system, image computer, mainframe computer system, workstation, network appliance, internet appliance, or other device. The subsystem(s) or system(s) may also include any suitable processor, such as a parallel processor. In addition, the subsystem(s) or system(s) may include a platform with high-speed processing and software, either as a standalone or as a networked tool.

The processor 708 may be disposed in or otherwise part of the system 700, respectively, or another device. In an example, the processor 708 may be part of a standalone control unit or in a centralized quality control unit. Multiple processors 708 may be used.

The processor 708 may be implemented in practice by any combination of hardware, software, and firmware. In addition, its functions as described herein may be performed by one unit, or divided up among different components, each of which may be implemented in turn by any combination of hardware, software and firmware. Program code or instructions for the processor 708 to implement various methods and functions may be stored in readable storage media, such as a memory in an electronic data storage unit or other memory.

If the system 700 includes more than one processor 708 then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media. Two or more of such subsystems may also be effectively coupled by a shared computer-readable storage medium (not shown).

The processor 708 may be configured to perform a number of functions using the output of the system 700, respectively, or other output. For instance, the processor 708 may be configured to send the output to an electronic data storage unit or another storage medium. The processor 708 may be further configured as described herein.

The processor 708 may be part of a defect review system, an inspection system, a metrology system, or some other type of system. Thus, the embodiments disclosed herein describe some configurations that can be tailored in a number of manners for systems having different capabilities that are more or less suitable for different applications.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media. Two or more of such subsystems may also be effectively coupled by a shared computer-readable storage medium (not shown).

The processor 708 may be configured according to any of the embodiments described herein. The processor 708 also may be configured to perform other functions or additional steps using the output of the system 700, respectively, or using images or data from other sources.

The processor 708 may be communicatively coupled to any of the various components or sub-systems of system 700, respectively, in any manner known in the art. Moreover, the processor 708 may be configured to receive and/or acquire data or information from other systems (e.g., inspection results from an inspection system such as a review tool, a remote database including design data and the like) by a transmission medium that may include wired and/or wireless portions. In this manner, the transmission medium may serve as a data link between the processor 708 and other subsystems of the system 700, respectively, or systems external to system 700, respectively.

The processor 708 is in electronic communication with a metrology tool, or inspection tool, such as system 700. For example, the processor 708 may be configured to perform embodiments of the method 1100.

An additional embodiment relates to a non-transitory computer-readable medium storing program instructions executable on a controller for performing a computer-implemented method as disclosed herein. In particular, as shown in FIG. 7, processor 708 may include an electronic data storage unit or other storage medium that may contain non-transitory computer-readable medium that includes program instructions executable on the processor 708. The computer-implemented method may include any step(s) of any method(s) described herein, including method 1100.

Program instructions implementing methods such as those described herein may be stored on computer-readable medium, such as in the electronic data storage unit or other storage medium. The computer-readable medium may be a storage medium such as a magnetic or optical disk, a magnetic tape, or any other suitable non-transitory computer-readable medium.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes (MFC), Streaming SIMD Extension (SSE), or other technologies or methodologies, as desired.

EXPERIMENTATION

Data with noise can impair the performance of deconvolution algorithms. Consider again the approach taken above, but with noise added to the data. If the noise is orders of magnitude smaller than the data, then deconvolution will operate properly. However, if the noise is on the same order as the data, deconvolution will generally amplify the noise and the resulting signal will be unusable. Thus, the signal to noise ratio of each acquired spectra must be carefully considered for embodiments of the present disclosure to yield an acceptable result. Consider the spectra shown in FIGS. 16-19 below, in which data were simulated with noise typical of the sensor used in a spectrometer. The total signal acquisition time was held constant, divided among $\Phi$=2, 4, 8 and 16 spectral sub-samples to be interleaved.

Figure 17:
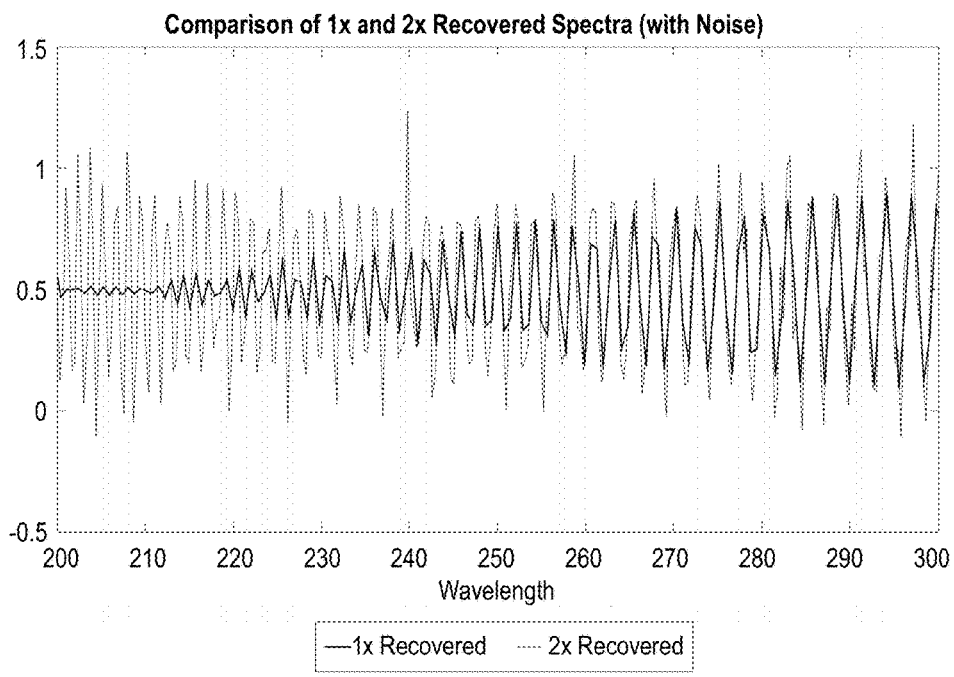
FIG. 17 is a comparison of 1× and 2× recovered spectra.
Figure 18:
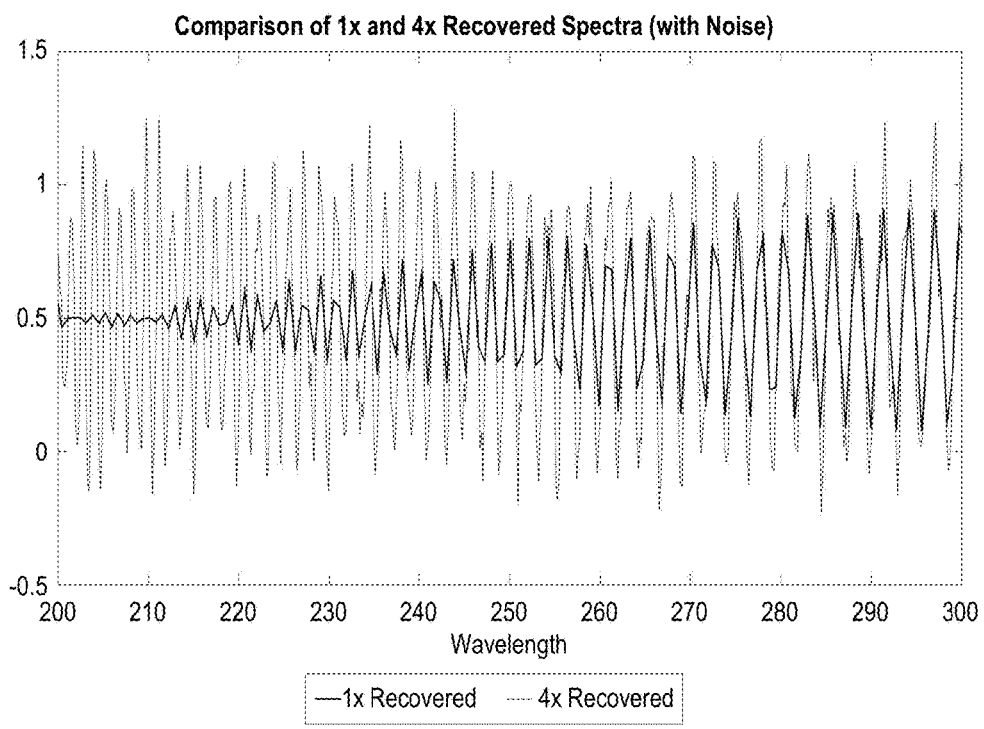
FIG. 18 is a comparison of 1× and 4× recovered spectra.
Figure 19:
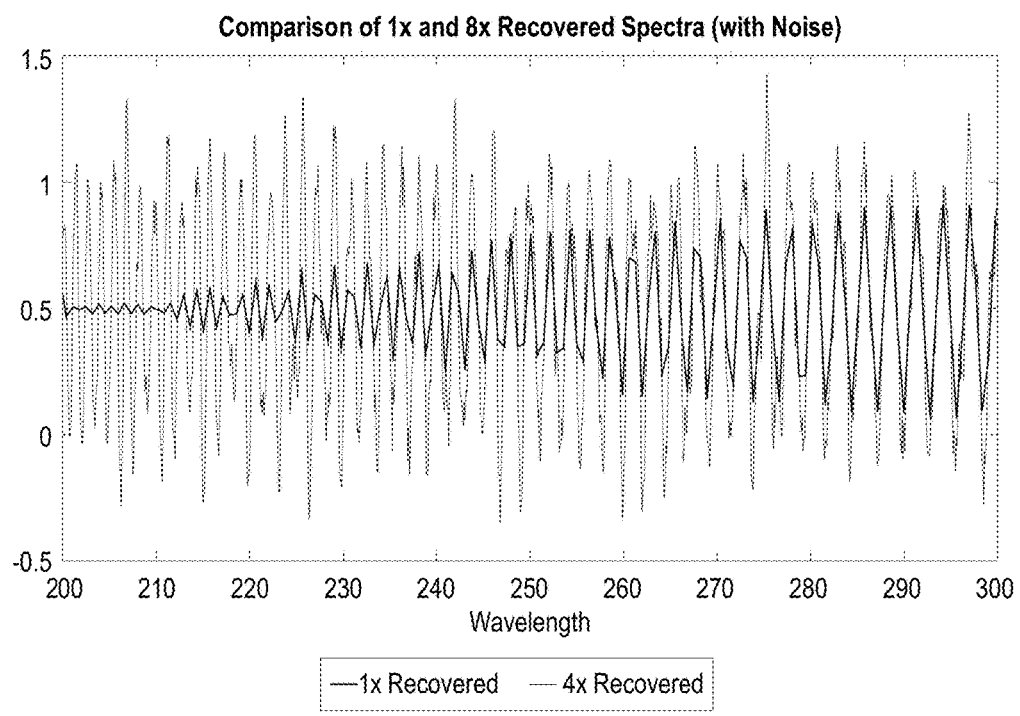
FIG. 19 is a comparison of 1× and 8× recovered spectra.
Figure 20:
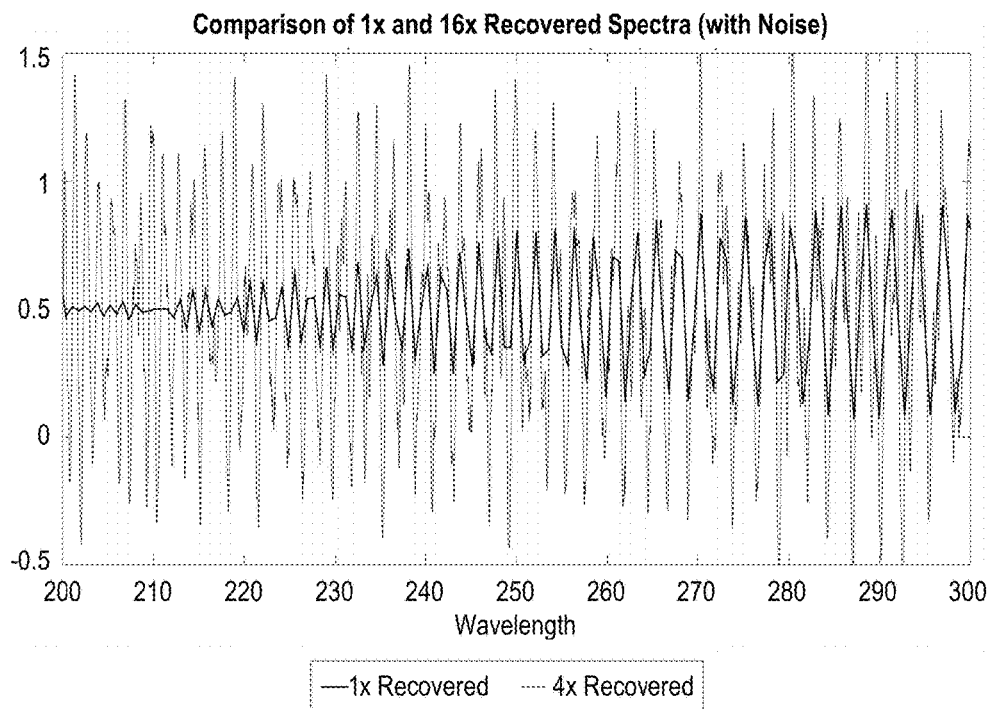
FIG. 20 is a comparison of 1× and 16× recovered spectra.

FIGS. 17-18 show this comparison of spectra recovered by embodiments of the present disclosure to the spectra recovered at $\Phi$=1. FIG. 17 shows a comparison of the recovered spectrum at $\Phi$=2 according to embodiments of the present disclosure compared to the spectrum recovered in accordance with conventional methods. This was much better than the $\Phi$=1 sampling approach, but the recovered spectra underestimates spectra amplitude between 0-1. FIG. 18 shows a comparison of the recovered spectrum at $\Phi$=4 according to embodiments of the present disclosure compared to the spectrum recovered in accordance with conventional methods. This was the performance with the most modest overshoot and undershoot. FIG. 19 shows a comparison of the recovered spectrum at $\Phi$=8 according to embodiments of the present disclosure compared to the spectrum recovered in accordance with conventional methods. The recovered spectrum in FIG. 19 depicts clear overshooting, but similar amplitude to that of FIG. 17. FIG. 20 shows a comparison of the recovered spectrum at $\Phi$=16 according to embodiments of the present disclosure compared to the spectrum recovered in accordance with conventional methods. This was an overshoot, which would likely not render an acceptable result.

The number of interleaved samples and the noise in each sample may need to be carefully balanced. If too few interleaved samples are chosen, the original spectrum may not be properly recovered. If too many interleaved samples are chosen, noise amplification can dominate the result, rendering it unusable. Several approaches are apparent, which can be considered to mitigate this problem. First, a less noisy sensor can be used. Second, a more sophisticated deconvolution algorithm can be used, such as the Wiener deconvolution, which is designed to work with noisy data. Third, increasing the acquisition time for each individual signal acquired can decrease noise. Other approaches may assist as well.

The third approach has the undesirable side effect of increasing total acquisition time, which may reduce the overall throughput of a semiconductor tool. However, thick-film and 3D-Flash use-cases are difficult problems. A high-noise, low-resolution signal is of little value, no matter how fast the tool can acquire them. In such cases, trading throughput for measurement quality may be an acceptable choice.

Figure 21:
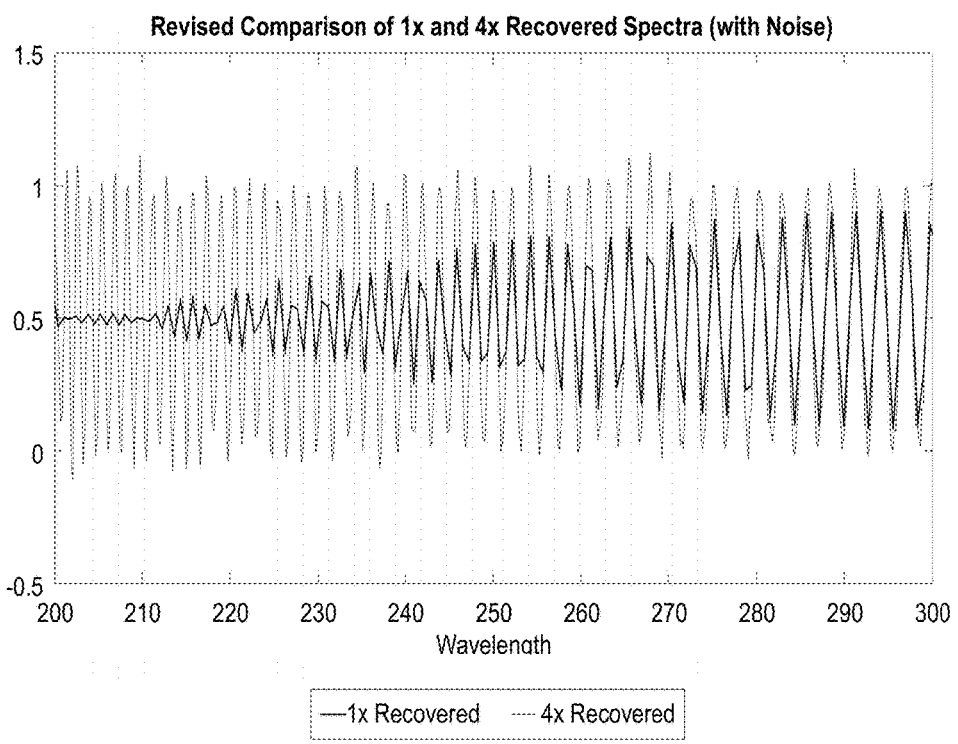
FIG. 21 is a revised comparison of 1× and 4× recovered spectra.

FIG. 21 depicts an example where the acquisition time for each interleaved spectra was increased by a factor of four, which approximately improves the signal to noise by a factor of two. With this configuration, excellent recovery of the original spectra is observed despite the introduction of sensor noise.

Systems, methods, and apparatuses according to the present disclosure overcome the aliasing issue when pixel size is large compared to the spectral signal frequency. They yield a high-resolution signal for processing by the computing engine. Further, they enable the use of deconvolution to reconstruct the original spectral signal via deconvolution pixel array quantization from the spectrum and deconvolution of a high-resolution rendition of the optical point spread function of the spectrum.

The steps of the method described in the various embodiments and examples disclosed herein are sufficient to carry out the methods of the present invention. Thus, in an embodiment, the method consists essentially of a combination of the steps of the methods disclosed herein. In another embodiment, the method consists of such steps.

Although the present disclosure has been described with respect to one or more particular embodiments, it will be understood that other embodiments of the present disclosure may be made without departing from the scope of the present disclosure.

What is claimed is:

1. A variable resolution spectrometer, comprising:
an optical system configured to transform rays, including:
a diffraction grating,
a steering mirror,
a stage, and
an actuator configured to move one of the stage, diffraction grating, or steering mirror according to a movement regime to vary an incidence of the rays on the stage, the movement regime having a start position and an end position;
a sensor array disposed on the stage including a plurality of pixel columns, each pixel column having at least one pixel, wherein the sensor array is configured to receive the rays incident from the optical system at a plurality of measurement locations to obtain a plurality of ray spectra; and
a processor electrically connected to the sensor array, wherein the processor is configured to:
receive the ray spectra,
interleave the ray spectra to yield an interleaved spectrum, and deconvolve a point spread function corresponding to the optical system from the interleaved spectrum to yield a recovered digitized spectrum.

2. The variable resolution spectrometer of claim 1, wherein the actuator is a piezo-actuator, a servo motor, or a stepper motor.

3. The variable resolution spectrometer of claim 1, wherein:
the stage is moved by the actuator; and
the movement regime is incremental translation, wherein:
the stage is translatably moved in one or more increments along a linear path from the start position to the end position, and
each of the increments has a start point and an end point separated by an incremental linear distance that is less than a total linear distance between the start position and the end position.

4. The variable resolution spectrometer of claim 1, wherein:
the stage is moved by the actuator; and
the movement regime is continuous translation, wherein the stage is translatably moved substantially continuously along a linear path from the start position to the end position.

5. The variable resolution spectrometer of claim 1, wherein:
the stage is moved by the actuator; and
the movement regime is incremental rotation, wherein:
the stage is rotatably moved in one or more increments along an arcuate path from the start position to the end position, and
each of the increments has a start point and an end point separated by an incremental arc length that is less than a total arc length between the start position and the end position.

6. The variable resolution spectrometer of claim 1, wherein:
the stage is moved by the actuator; and
the movement regime is continuous rotation, wherein the stage is rotatably moved substantially continuously along an arcuate path from the start position to the end position.

7. The variable resolution spectrometer of claim 1, wherein two measurement locations in the plurality of measurement locations are separated by a distance less than a pixel breadth.

8. The variable resolution spectrometer of claim 1, wherein the sensor array is a charge-coupled device.

9. The variable resolution spectrometer of claim 1, wherein:
the diffraction grating is moved by the actuator; and
the movement regime is incremental translation, wherein:
the diffraction grating is translatably moved in one or more increments along a linear path from the start position to the end position, and
each of the increments has a start point and an end point separated by an incremental linear distance that is less than a total linear distance between the start position and the end position.

10. A method for recovering a digitized spectrum, comprising:
providing an optical system configured to transform rays, including:
a diffraction grating,
a steering mirror,
an actuator, and
a stage; and
executing a scan operation, the scan operation comprising:
moving, using the actuator, one of the stage, diffraction grating, or steering mirror according to a movement regime to vary an incidence of the rays on the stage, the movement regime having a start position and an end position, and
sensing, using a sensor array disposed on the stage including a plurality of pixel columns rays incident on the sensor array from the optical system at a plurality of measurement locations to obtain a plurality of ray spectra, wherein each of the pixel columns has at least one pixel; and
using a processor:
receiving the ray spectra,
interleaving the ray spectra to yield an interleaved spectrum, and
deconvolving a point spread function corresponding to the optical system from the interleaved spectrum to yield a recovered digitized spectrum.

11. The method of claim 10, wherein the actuator is a piezo-actuator, a servo motor, or a stepper motor.

12. The method of claim 10, wherein:
the stage is moved by the actuator; and
the movement regime is incremental translation, wherein:
the stage is translatably moved in one or more increments along a linear path from the start position to the end position, and
each of the increments has a start point and an end point separated by an incremental linear distance that is less than a total linear distance between the start position and the end position.

13. The method of claim 10, wherein:
the stage is moved by the actuator; and
the movement regime is continuous translation, wherein the stage is translatably moved substantially continuously along a linear path from the start position to the end position.

14. The method of claim 10, wherein:
the stage is moved by the actuator; and
the movement regime is incremental rotation, wherein:
the stage is rotatably moved in one or more increments along an arcuate path from the start position to the end position, and
each of the increments has a start point and an end point separated by an incremental arc length that is less than a total arc length between the start position and the end position.

15. The method of claim 10, wherein:
the stage is moved by the actuator; and
the movement regime is continuous rotation, wherein the stage is rotatably moved substantially continuously along an arcuate path from the start position to the end position.

16. The method of claim 10, wherein two measurement locations in the plurality of measurement locations are separated by a distance less than a pixel breadth.

17. The method of claim 10, wherein the sensor array is a charge-coupled device.

18. The method of claim 10, wherein:
the diffraction grating is moved by the actuator; and
the movement regime is incremental translation, wherein:
the diffraction grating is translatably moved in one or more increments along a linear path from the start position to the end position, and
each of the increments has a start point and an end point separated by an incremental linear distance that is less than a total linear distance between the start position and the end position.

19. The method of claim 10, wherein:
the diffraction grating is moved by the actuator; and
the movement regime is continuous translation, wherein the diffraction grating is translatably moved substantially continuously along a linear path from the start position to the end position.

20. A non-transitory computer-readable storage medium, comprising one or more programs for executing the following steps on one or more computing devices:
receive ray spectra obtained from rays incident on a sensor array including a plurality of pixel columns, each of the pixel columns having at least one pixel, wherein the sensor array is disposed on a stage from an optical system comprising the stage, a diffraction grating and a steering mirror, wherein the stage, diffraction grating, or steering mirror is moved, using an actuator according to a movement regime to vary the incidence of rays on the stage, and wherein the movement regime has a start position and an end position;
interleave the ray spectra to yield an interleaved spectrum; and
deconvolve a point spread function corresponding to the optical system from the interleaved spectrum to yield a recovered digitized spectrum.

\* \* \* \* \*